(12) United States Patent
Lee et al.

(10) Patent No.: US 9,494,508 B2
(45) Date of Patent: Nov. 15, 2016

(54) PARTICULATE MATTER SENSOR UNIT

(71) Applicants: Hyundai Motor Company, Seoul (KR); SNU R&DB FOUNDATION, Seoul (KR)

(72) Inventors: Jin Ha Lee, Seoul (KR); Sera Lim, Mokpo-si (KR); Kuk-jin Chun, Seoul (KR); Junyong Lee, Seoul (KR); Kyoung doug Min, Seoul (KR); Seounghyeon Lee, Goyang-si (KR); Young Jae Kim, Busan (KR)

(73) Assignees: Hyundai Motor Company, Seoul (KR); SNU R&DB FOUNDATION, Seoul (KR)

( * ) Notice: Subject to any disclaimer, the term of this patent is extended or adjusted under 35 U.S.C. 154(b) by 288 days.

(21) Appl. No.: 14/145,169

(22) Filed: Dec. 31, 2013

(65) Prior Publication Data
US 2015/0020576 A1 Jan. 22, 2015

(30) Foreign Application Priority Data

Jul. 18, 2013 (KR) .......................... 10-2013-0084909

(51) Int. Cl.
*G01N 37/00* (2006.01)
*G01N 15/06* (2006.01)
*G01N 15/00* (2006.01)

(52) U.S. Cl.
CPC ...... *G01N 15/0656* (2013.01); *G01N 15/0606* (2013.01); *G01N 2015/0046* (2013.01); *G01N 2015/0681* (2013.01)

(58) Field of Classification Search
CPC ...................... G01N 15/0656; G01N 15/0606
USPC ......................................................... 73/28.02
See application file for complete search history.

(56) References Cited

U.S. PATENT DOCUMENTS

2011/0192211 A1* 8/2011 Yokoi ................ G01N 27/4163
73/1.06

FOREIGN PATENT DOCUMENTS

KR 10-2013-0065409 6/2013

* cited by examiner

*Primary Examiner* — Hezron E Williams
*Assistant Examiner* — Rodney T Frank
(74) *Attorney, Agent, or Firm* — Morgan, Lewis & Bockius LLP

(57) ABSTRACT

A particulate matter sensor unit may include a sensor portion of an electrostatic induction type that may be reacted when a particulate matter having electric charge may be passing the vicinity thereof, a protection pad that the sensor portion may be bonded on one side thereof through a conductive paste, an heater electrode that may be formed on the protection pad and burns the particulate matters that may be disposed on the sensor portion to eliminate them, and a sensor electrode that may be formed on the protection pad to transfer a signal that may be generated by the sensor portion to an outside.

7 Claims, 7 Drawing Sheets

PARTICULATE MATTER SENSOR UNIT

CROSS-REFERENCE TO RELATED APPLICATION

The present application claims priority to Korean Patent Application No. 10-2013-0084909 filed on Jul. 18, 2013, the entire contents of which is incorporated herein for all purposes by this reference.

BACKGROUND OF THE INVENTION

1. Field of the Invention

The present invention is related to a particulate matter sensor unit that effectively detects particulate matters, sustains a sensitivity of a sensor, and improves overall mechanical strength.

2. Description of Related Art

A particulate filter (PF) for reducing an exhaust gas is applied to a vehicle. A differential pressure sensor is used to sense the amount of an exhaust gas collected by the particulate filter.

The particulate filter can be selectively applied to all internal combustion engines, such as a diesel vehicle, a gasoline vehicle, and a gas vehicle.

In the future, in accordance with exhaust gas control, the sensing precision of particulate matter collected by a diesel particulate filter by using the existing differential pressure sensor can be lowered, and it is not easy to sense damage to the diesel particulate filter.

Meanwhile, research into a sensor for sensing particulate matter continues to be carried out, research is being carried out in order to maintain the sensitivity of a sensor by removing particulate matter when the particulate matter is adhered to the sensor, and research is also is being carried out so as to improve the strength of a sensor portion.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a particulate matter sensor unit having advantages of reinforcing strength of a sensor portion thereof, reducing cost, and increasing production amount by improving the productivity in a production process.

In an aspect of the present invention, a particulate matter sensor unit, may include a sensor portion of an electrostatic induction type that is reacted when a particulate matter having electric charge is passing a vicinity thereof, a protection pad that the sensor portion is bonded on a side of the protection pad through a conductive paste, an heater electrode that is formed on the protection pad and is configured to burn the particulate matter that is disposed on the sensor portion to eliminate particulate matter, and a sensor electrode that is formed on the protection pad to transfer a signal that is generated by the sensor portion to an outside.

The sensor portion may include a sensor body that a sensor protrusion portion of silicon material is formed on an upper side surface thereof, an insulating layer that covers an upper side and a lower side of the sensor body, and a connection electrode that connects the sensor body with the sensor electrode through a part that the insulating layer is not formed.

Wherein the sensor electrode is formed at an upper surface of the protection pad and the heater electrode is formed at a lower surface of the protection pad, wherein the conductive paste is applied on a side of the upper surface of the protection pad to cover a part of the sensor electrode, and wherein the sensor portion is bonded on the conductive paste to be fixed on the upper surface of the protection pad.

The sensor portion or the heater electrode may include at least one of Pt, Mo, and W.

The protection pad may include ceramic material.

The sensor body is fabricated by etching silicon wafer.

The insulating layer is made by $SiO_2$ or $Si_3O_4$.

The ceramic material may include $Si_3O_4$, mullite, or glass ceramic.

As described above, a particulate matter sensor unit according to an exemplary embodiment of the present invention can supplement the strength of a sensor portion in which a protection pad on which the sensor portion is mounted is formed as a silicon wafer.

Also, because a silicon wafer is fabricated through a semiconductor production process and the silicon wafer is mounted on a protection pad through a conductive paste, production cost can be reduced and the production amount can be increased.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention (s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

An exemplary embodiment of the present invention will hereinafter be described in detail with reference to the accompanying drawings.

Figure 1:
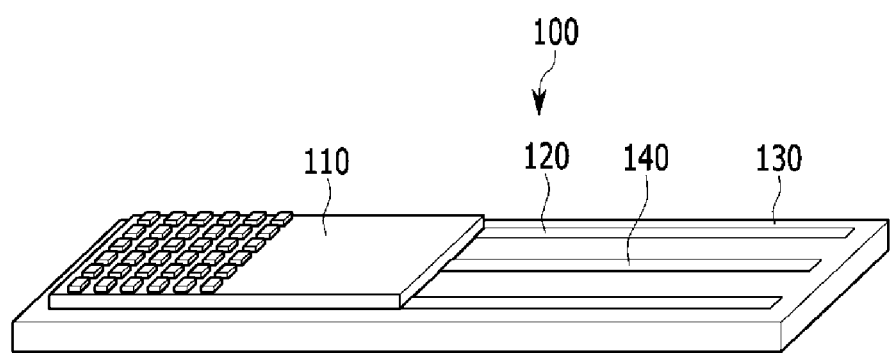
FIG. 1 is a partial perspective view of a sensor unit according to an exemplary embodiment of the present invention.

FIG. 1 is a partial perspective view of a sensor unit according to an exemplary embodiment of the present invention.

Referring to FIG. 1, a sensor unit 100 includes a sensor portion 110, a heater electrode 120, a protection pad 130, and a sensor electrode 140.

When a particulate matter having electric charge is passing a vicinity of the sensor portion 110, the sensor portion 110 is reacted to generate electric signal.

The protection pad 130 is ceramic material, the heater electrode 120 is formed thereon, and the heater electrode 120 heats particulate matters that is disposed on the sensor portion 110 to eliminate them. The sensor electrode 140 performs a function that transfers a signal that is generated from the sensor portion 110.

Figure 2:
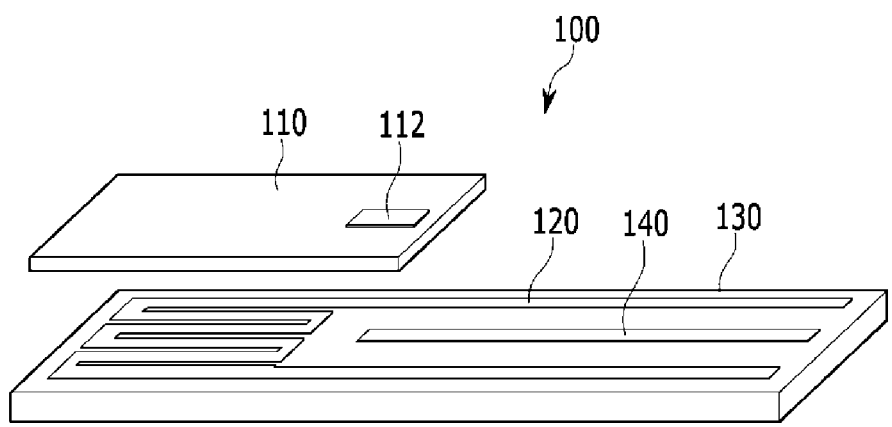
FIG. 2 is a partial exploded perspective view in a sensor unit according to an exemplary embodiment of the present invention.

FIG. 2 is a partial exploded perspective view in a sensor unit according to an exemplary embodiment of the present invention.

Referring to FIG. 2, the heater electrode 120 is formed on one side of an upper surface of the protection pad 130 of ceramic material along a zigzag shape and the sensor electrode 140 is formed at a central portion of an upper surface of the protection pad 130. And, a connection electrode 112 that is connected to the sensor electrode 140 is formed at a rear surface of the sensor portion 110.

In an exemplary embodiment of the present invention, because the sensor portion 110 that is made by silicon and insulating material is bonded on the protection pad 130 that is ceramic substrate, the function of the sensor portion 110 is preserved and strength and rigidity can be improved.

And, the conductive paste 300 is selected by considering a thermal expansion coefficient between silicon that is material of the sensor portion 110 and ceramic that is material of the protection pad 130 so as to bond the sensor portion 110 on the protection pad 130.

Because the sensor portion 110 puts up with a temperature of about 650 Celsius degrees, the conductive paste 300 is to be made of alloy material having a high temperature resistance and a bonding art such as flip chip bonding, screen printing, or electroplating can be applied as a bonding method.

Figure 3:
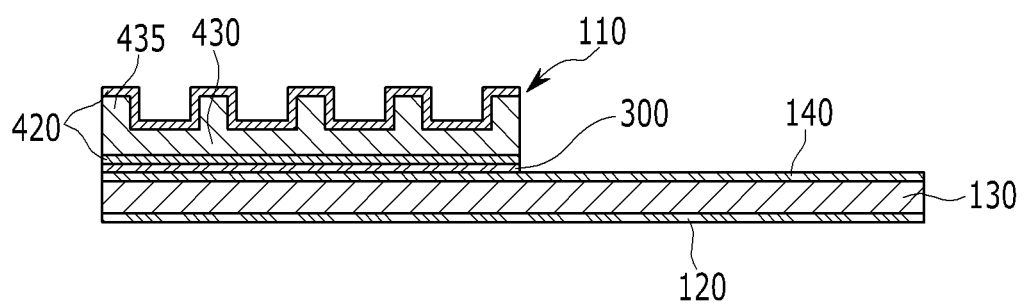
FIG. 3 is a cross-sectional view of a sensor unit according to an exemplary embodiment of the present invention.

FIG. 3 is a cross-sectional view of a sensor unit according to an exemplary embodiment of the present invention.

Referring to FIG. 3, the sensor portion 110 of the sensor unit 100 includes a sensor body 430 that is formed at a central portion as silicon material and a sensor protrusion portion 435 is convexly formed at an upper surface thereof and an insulating layer 420 that is formed at an upper surface and a lower surface of the sensor body 430.

The sensor electrode 140 is formed on an upper surface of the protection pad 130 and the heater electrode 120 is formed on a lower surface of the protection pad 130. In an exemplary embodiment of the present invention, the heater electrode 120 is formed at an upper surface of the protection pad 130 near the sensor electrode 140.

The sensor portion 110 is bonded on a left side of an upper surface of the protection pad 130 and the conductive paste 300 is interposed between the sensor portion 110 and the protection pad 130.

And, the sensor body 430 of the sensor portion 110 is connected to the sensor electrode 140 through the connection electrode 112 and the conductive paste 300.

Figure 4:
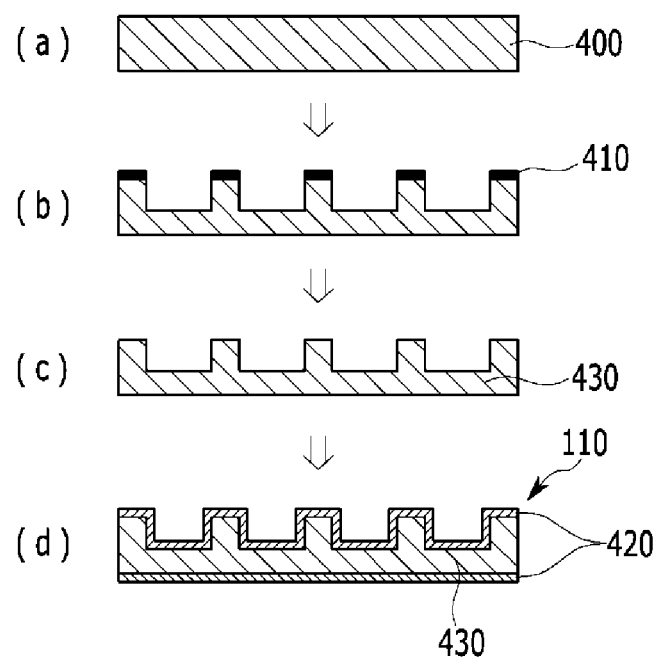
FIG. 4 is a process diagram showing a manufacturing method of a sensor portion that is provided on a sensor unit according to an exemplary embodiment of the present invention.

FIG. 4 is a process diagram showing a manufacturing method of a sensor portion that is provided on a sensor unit according to an exemplary embodiment of the present invention.

Referring to FIG. 4, a silicon wafer 400 is washed in a (a), and after a photo resist 410 is formed on the silicon wafer 400 and an etching process is performed to form a protrusion portion on the wafer in a (b).

The photo resist 410 is eliminated in (c), and an insulating layer 420 is formed at an upper surface and a lower surface of the wafer in a (d). In an exemplary embodiment of the present invention, the insulating layer 420 can include $SiO_2$ or $Si_3O_4$.

Figure 5:
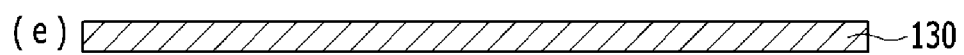
FIG. 5 is a process diagram showing a manufacturing method of a heater electrode that is provided on a sensor unit according to an exemplary embodiment of the present invention.
Figure 5:
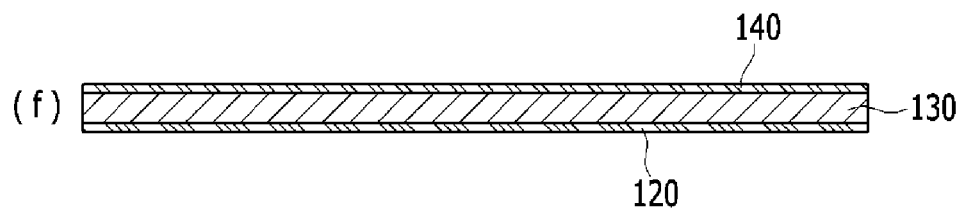
Figure 5:
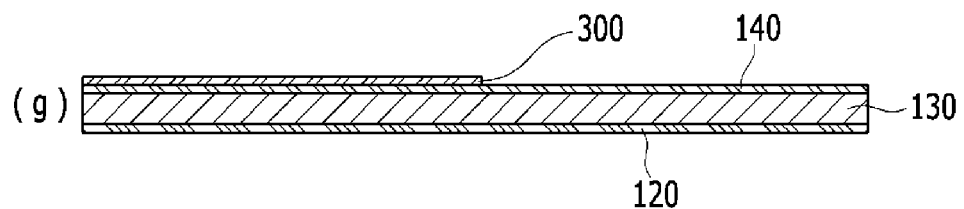
Figure 5:
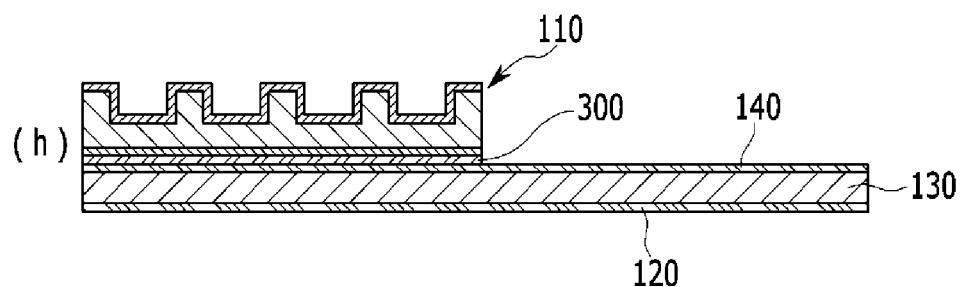

FIG. 5 is a process diagram showing a manufacturing method of a heater electrode that is provided on a sensor unit according to an exemplary embodiment of the present invention.

Referring to FIG. 5, the protection pad 130 that is ceramic material is washed to be prepared in (e), and the sensor electrode 140 is formed at an upper surface of the protection pad 130 and the heater electrode 120 is formed at a lower surface thereof in a (f).

The conductive paste 300 is applied to one side of an upper surface of the protection pad 130 in a (g), and the sensor portion 110 is bonded on the conductive paste 300 in a (h).

The protection pad 130 as a ceramic substrate can include $Si_3N_4$, mullite, or glass ceramic, and the heater electrode 120 can include Pt, Mo, or W. The sensor electrode 140 can include Pt, Mo, or W.

Figure 6:
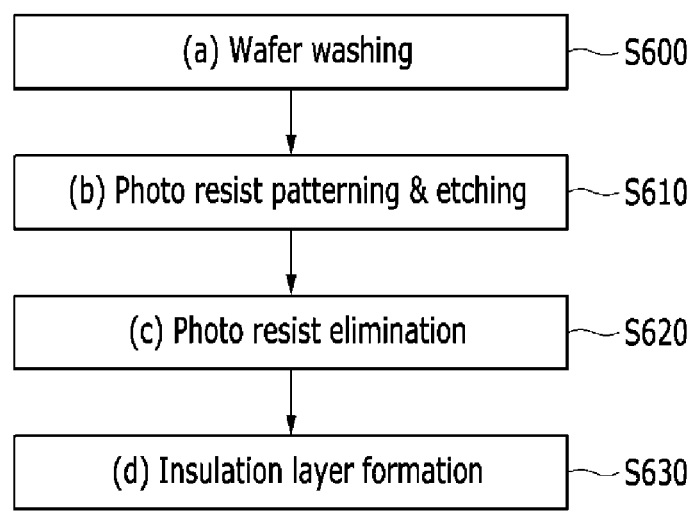
FIG. 6 is a flowchart showing a manufacturing method of a sensor portion that is provided on a sensor unit according to an exemplary embodiment of the present invention.

FIG. 6 is a flowchart showing a manufacturing method of a sensor portion that is provided on a sensor unit according to an exemplary embodiment of the present invention.

Referring to FIG. 6, a silicon wafer 400 is washed in a 5600, a photo resist 410 is patterned on an upper surface of the silicon wafer 400 M a S610, the photo resist 410 is eliminated in a S620, and the insulating layer 420 is formed on an upper surface and a lower surface to form the sensor portion 110 in a S630.

Figure 7:
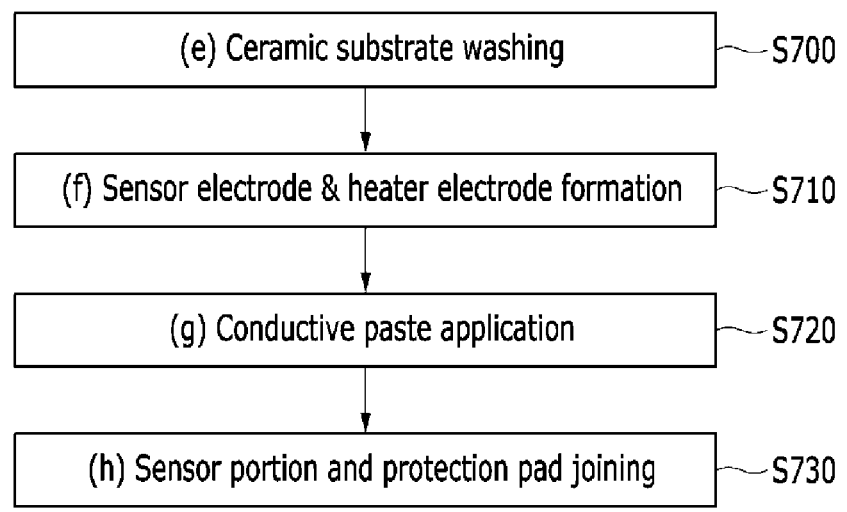
FIG. 7 is a flowchart showing a manufacturing method of a heater electrode that is provided on a sensor unit according to an exemplary embodiment of the present invention.

FIG. 7 is a flowchart showing a manufacturing method of a heater electrode that is provided on a sensor unit according to an exemplary embodiment of the present invention.

Referring to FIG. 7, the protection pad 130 as a ceramic substrate is washed in a S700, the heater electrode 120 and the sensor electrode (140, contact pad) is formed on the protection pad 130 in a 5710, the conductive paste 300 is applied to an upper surface of the protection pad 130 in a S720, and the sensor portion 110 is bonded on the protection pad 130 through the conductive paste 300 in a S730.

For convenience in explanation and accurate definition in the appended claims, the terms "upper", "lower", "inner"

and "outer" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. They are not intended to be exhaustive or to limit the invention to the precise forms disclosed, and obviously many modifications and variations are possible in light of the above teachings as well as various alternatives and modifications thereof It is intended that the scope of the invention be defined by the Claims appended hereto and their equivalents.

What is claimed is:

1. A particulate matter sensor unit, comprising:
   a sensor portion of an electrostatic induction type that is reacted when a particulate matter having electric charge is passing a vicinity thereof;
   a protection pad that the sensor portion is bonded on a side of the protection pad through a conductive paste;
   an heater electrode formed on the protection pad and configured to burn the particulate matter disposed on the sensor portion to eliminate particulate matter; and
   a sensor electrode formed on the protection pad to transfer a signal generated by the sensor portion to an outside,
   wherein the sensor portion includes:
   a sensor body, wherein the sensor body is disposed on the sensor electrode and a sensor protrusion portion of silicon material is formed on an upper side surface of the sensor body, and;
   an insulating layer covering an upper side and a lower side of the sensor body; and
   a connection electrode connecting the sensor body with the sensor electrode through a part that the insulating layer is not formed.

2. The particulate matter sensor unit of claim 1, wherein the sensor body is fabricated by etching silicon wafer.

3. The particulate matter sensor unit of claim 1, wherein the insulating layer is made by SiO2 or Si3O4.

4. The particulate matter sensor unit of claim 1,
   wherein the sensor electrode is formed at an upper surface of the protection pad and the heater electrode is formed at a lower surface of the protection pad,
   wherein the conductive paste is applied on a side of the upper surface of the protection pad to cover a part of the sensor electrode, and
   wherein the sensor portion is bonded on the conductive paste to be fixed on the upper surface of the protection pad.

5. The particulate matter sensor unit of claim 1, wherein the sensor portion or the heater electrode includes at least one of Pt, Mo, and W.

6. The particulate matter sensor unit of claim 1, wherein the protection pad includes ceramic material.

7. The particulate matter sensor unit of claim 6, wherein the ceramic material includes Si3O4, mullite, or glass ceramic.

* * * * *